United States Patent [19]

Esser

[11] Patent Number: 5,146,928
[45] Date of Patent: Sep. 15, 1992

[54] SAMPLING DEVICE FOR COLLECTING MICROBIOLOGICAL BIOPSY SPECIMEN

[76] Inventor: Theodor Esser, 21 William Penn Dr., Stony Brook, N.Y. 11790

[21] Appl. No.: 828,370

[22] Filed: Jan. 30, 1992

[51] Int. Cl.$^5$ ............................................. A61B 10/00
[52] U.S. Cl. ...................................... 128/756; 15/206
[58] Field of Search ............... 128/749, 750, 751, 754, 128/756, 757, 759, 180; 606/180; 604/282; 15/206

[56] References Cited

U.S. PATENT DOCUMENTS

| | | | |
|---|---|---|---|
| 2,955,592 | 12/1955 | MacLean | 128/756 |
| 3,521,620 | 7/1970 | Cook . | |
| 3,613,664 | 10/1971 | Willson et al. . | |
| 3,799,151 | 3/1974 | Fukaumi et al. . | |
| 4,235,244 | 11/1980 | Abele et al. | 128/756 X |
| 4,682,606 | 7/1987 | DeCaprio . | |
| 4,776,346 | 10/1988 | Beraha et al. . | |
| 4,785,826 | 11/1988 | Ward . | |
| 4,923,462 | 5/1990 | Stevens | 606/180 X |
| 4,936,312 | 6/1990 | Tsukagoshi . | |
| 4,955,862 | 9/1990 | Sepetka . | |
| 4,961,430 | 10/1990 | Sheahon . | |
| 4,986,279 | 1/1991 | O'Neill . | |
| 4,991,588 | 2/1991 | Pflueger et al. . | |

OTHER PUBLICATIONS

"Mill-Rose Gastrointestinal Cytology Brush", Advertisement Brochure (published prior to 1991), distributed by Mill-Rose Laboratories, Inc.

Primary Examiner—Kyle L. Howell
Assistant Examiner—Samuel Gilbert
Attorney, Agent, or Firm—Scully, Scott, Murphy & Presser

[57] ABSTRACT

A specimen sampling device for the collection of microbiological biopsy specimen from a body cavity and, more particularly, a device which incorporates a cytology brush which is readily introducible into the biopsy channel of an endoscope. In particular, the cytology brush is especially adapted for brushing and thereby obtaining microbiological biopsy specimen from areas of the gastrointestinal tract which are difficult to reach. A flexible stainless steel sheath constituted from helical coils is encompassed by a plastic sleeve which is adhered thereto, such plastic sleeve preferably being constituted from teflon or the like, and in which a proximal end of the tubing includes structure cooperative with a manipulating component attached to a composite operating wire structure for a cytology brush located at a distal end thereof and extending through the sheath so as to be able to longitudinally displace and rotate the wire and resultingly the cytology brush in a controlled mode. For this purpose, the outer sleeve consisting of the plastic or teflon tubing extends a predetermined axial length beyond the distal end of the inner sheath constituted from the stainless steel helical coils, so as to form a cylindrical section of larger diameter than the internal diameter of the helical coil flexible member, and with the cytology brush, in the retracted position thereof entirely located within the confines of this cylindrical section.

13 Claims, 2 Drawing Sheets

SAMPLING DEVICE FOR COLLECTING MICROBIOLOGICAL BIOPSY SPECIMEN

BACKGROUND OF THE INVENTION

1. Field of the Invention

The present invention relates to a specimen sampling device for the collection of microbiological biopsy specimen from a body cavity and, more particularly, relates to a device which incorporates a cytology brush which is readily introducible into the biopsy channel of an endoscope. In particular, the cytology brush is especially adapted for brushing and thereby obtaining microbiological biopsy specimen from areas of the gastrointestinal tract which are difficult to reach. Pursuant to another important aspect of the invention, the specimen sampling device incorporating the gastrointestinal cytology brush is of simple and inexpensive yet sturdy and reliably operable construction so at to render the brush readily disposable in a highly economical manner after only a single use.

Although numerous and widely varied types of biopsy specimen sampling devices for collecting microbiological specimen are currently known in the medical technology, particularly in conjunction with their use in endoscopes, these are either of generally complicated constructions which necessitate the manufacture and assembly of highly expensively produced components or; alternatively, are of such simple construction as to lack the sophistication and strength to enable them to be satisfactorily operated for their intended purposes. Thus, in particular, cytology brushes which are introduced into body cavities through endoscopes for the brushing and removal of microbiological biopsy samples from gastrointestinal tracts are subject to a number of limitations and disadvantages as currently employed in the state-of-the-technology.

Hereby, pursuant to a specific construction of a cytology brush as presently utilized for the obtaining of microbiological biopsy specimen, the structure of the sampling device incorporates an elongated flexible plastic tubing forming a sheath insertable into the biopsy channel of an endoscope, through which an operating wire is conducted from a proximal end mounting structure for effectuating longitudinal and rotational movement of the wire within the flexible sheath, and at a distal end of the sheath the wire has a cytology brush mounted thereon consisting of nylon bristles which, when the brush is extended outwardly beyond the distal end of the sheath is adapted to brush over and obtain microbiological biopsy specimen from the body cavity of a patient. Thereafter, the cytology brush with the microbiological biopsy specimen entrained in the bristles is withdrawn into the distal end of the plastic sheath, and the entire sampling device withdrawn from the body cavity through the endoscope. This type of construction, in which the outer diameter of the bristles of the cytology brush is dimensioned to be slightly larger than the internal diameter of the plastic sheath causes the brush bristles to assume a bend deviating from a radial orientation, and moreover, when retracted into the distal end of the sheath after obtaining the biopsy specimen, to be subject to some further bending of the extended bristles which may cause some of the entrained microbiological biopsy matter to be sprayed outwardly into the body cavity so as to become a source of infection in the patient. Moreover, when the cytology brush is extended from the distal end of the plastic sheath subsequent to withdrawal of the device from the endoscope in order to be able to examine the biopsy specimen, the exposure of bristles of the cytology brush may cause the bristles to expand and possibly spray out some biopsy matter entrained therein, thereby contaminating the laboratory and the analyzing personnel. Additionally, a cytology brush which has the outer plastic tubing sheath constructed from only a single tubing member and with a central wire is frequently subject to kinking when inserted into an endoscope, and moreover, rotation of the operating wire mounting the brush at its distal end becomes rather difficult and cannot be satisfactorily implemented in a controlled manner.

2. Discussion of the Prior Art

Although various attempts have been made which are intended to overcome difficulties encountered in the state-of-the-art as represented by the foregoing type of construction of a cytology brush, it is still subject to various disadvantages and drawbacks.

Abele, et al. U.S. Pat. No. 4,235,244 discloses a microbiological specimen sampling device which has a cytology brush mounted at the distal end of an operating wire adapted to be longitudinally displaced within a tubular plastic member. A second outer sleeve is mounted over the tubular plastic member and extends some distance beyond the leading or distal end which is adapted to be inserted through an endoscope into a body cavity, and which retains a plug which will protect the specimen sampling brush from contamination during introduction into the body cavity and is adapted to be ejected upon being pushed outwardly by an extending sampling brush. In this particular instance, the brush which is contained within the inner sleeve tubing is subject to the disadvantages of having its bristles bent and radially compressed, and thereafter expanded when pushed outwardly through the larger diameter section into the body cavity, and subsequent to obtaining microbiological biopsy specimen being again compressed when entering the inner tubular member upon retraction.

MacLean U.S. Pat. No. 2,955,592 discloses a diagnostic instrument which has a brush adapted to be inserted into a body cavity, and to be able to obtain microbiological biopsy samples for analysis. There is no disclosure of the brush being arranged in a specimen sampling device analogous to that contemplated by the present invention, particularly as described hereinbelow in more extensive detail.

Similarly, Tsukagoshi U.S. Pat. No. 4,936,312 discloses a body cavity inserting instrument having a brush for picking up and retaining microbiological samples which is attached to an operating wire enclosed within a helically-coiled outer sheathing. Also in this instance, there is no disclosure of the brush being extended and thereafter retracted after obtaining microbiological samples in a manner contemplated by the present invention.

SUMMARY OF THE INVENTION

In order to provide a novel microbiological biopsy specimen sampling device incorporating a cytology brush which enables the improved and hygienic obtention of microbiological biopsy specimen, such as from a gastrointestinal tract or the like, the present invention contemplates the provision of a device in which tubular flexible stainless steel sheath constituted from helical coils is encompassed by a plastic sleeve which is adhered thereto, such plastic sleeve preferably being constituted from teflon or the like, and in which a proximal end of the tubing includes structure cooperative with a manipulating component attached to an operating wire structure for a cytology brush located at a distal end thereof and extending through the sheath so as to be able to longitudinally displace and rotate the wire and resultingly the cytology brush in a controlled mode. For this purpose, the outer sleeve consisting of the plastic or teflon tubing extends a predetermined axial length beyond the distal end of the inner sheath constituted from the stainless steel helical coils, so as to form a cylindrical section of larger diameter than the internal diameter of the helical coil flexible member, and with the cytology brush, in the retracted position thereof entirely located within the confines of this cylindrical section. The longitudinal movement of the wire is calibrated relative to the outer sheathing such that upon implementing the forward or outward displacement of the cytology brush, at least a trailing end portion of the brush will remain within the cylindrical section extending beyond the inner helically-coiled sheath so as to form a guide during retraction of the brush subsequent to obtaining microbiological biopsy specimen from a body cavity.

Moreover, the operating wire for the brush in order to facilitate the controlled rotation thereof, is preferably constituted of a central twisted wire structure which is encompassed by a braided outer cable fastened to the central wire structure at the proximal and distal ends thereof to allow for a positive rotation of the brush by rotating the manipulating structure at the proximal end of the operating wire.

The outer diameter of the brush bristles is dimensioned so as to fit into the internal diameter of the outer plastic tubing or sleeve, such that upon retraction of the brush into the cylindrical section which extends beyond the distal end of the inner helically-coiled sheath, this will allow for the brush to be retracted without the bristles thereof collapsing or being bent. Moreover, the retractive movement of the brush into the cylindrical section is controlled or essentially limited in that the trailing end of the brush in the fully retracted position thereof contacts against the end surface of the flexible helically-coiled inner tubular sheath so as to provide indication to an operate of the device that the brush has been fully retracted into the cylindrical section.

The advantages of the foregoing inventive cytology brush structure over the art, among other advantages, resides in that the bristles of the cytology brush will not bend over or lie down in view of the presence of the larger diameter of the outer sleeve of plastic material which is fastened to the inner flexible tubing sheath forming the extended cylindrical section receiving the brush such that the radially oriented outwardly extending bristles of the brush enable an improved brushing and assumption of biopsy samples in a manner reducing potential risks of contamination.

Moreover, the bristles of the cytology brush are adapted to retain larger quantities of the microbiological biopsy specimen in view of the feature that the brush is not compressed when retracted the cylindrical section formed by the outer sleeve at the distal end beyond the inner sheath, and also when withdrawn from the endoscope subsequent to the sampling procedure and thereafter removed from the brush in a medical laboratory or the like for purposes of conducting a biopsy.

The utilization of the inner flexible tubular member or sheath consisting preferably of medical-grade stainless steel in the form of helical coils and encompassed by the plastic or teflon sleeve will also to a considerable extent prevent any kinking of the instrument when inserted into an endoscope. Additionally, novel composite construction of the kink-resistent operating wire structure which also is preferably constituted from stainless steel by having a braided outer cable encompassing an operating wire, and which are soldered together at opposite ends of the device, will also ensure that the brush can be easily rotated during the brushing and taking up of microbiological biopsy material from the body cavity of a patient in a controlled manner through simple rotation of the manipulating structure at the proximal end of the sampling device externally of the endoscope. This imparts a relatively sturdy construction for the specimen sampling device incorporating the cytology brush which, although simple in construction and highly dependable in its functioning, will result in an inexpensively produced structure rendering the entire device economically disposable after only a single use; which aspect is highly desirable in view of the considerable risks to patients of being subjected to potential exposure to serious and even life-threatening infection with the AIDS Virus (Acquired Immunity Deficiency Syndrome) or hepatitis B viruses by reuse of such a device, wherein even current procedures in the sterilizing of such cytology brushes may not be always adequate to destroy viruses or may possibly even raise doubts as to the efficacy of the sterilizing solutions.

Accordingly, it is a basic object of the present invention to provide a novel sampling device for the obtention of microbiological biopsy specimen from the body cavity of a patient.

It is another object of the present invention to provide a novel specimen sampling device incorporating a gastrointestinal cytology brush of novel design and construction which is utilizable in an endoscope for the brushing and obtention of microbiological biopsy matter in the body cavity of a patient in the absence of any danger of spraying biopsy matter interiorly of the body cavity or into the environment subsequent to the withdrawal of the device from the endoscope and in a medical laboratory.

BRIEF DESCRIPTION OF THE DRAWINGS

The foregoing advantages and other objects of the invention may now be more readily ascertained from the following detailed description of an exemplary embodiment thereof, taken in conjunction with the accompanying drawings; in which.

DETAILED DESCRIPTION

Figure 1:
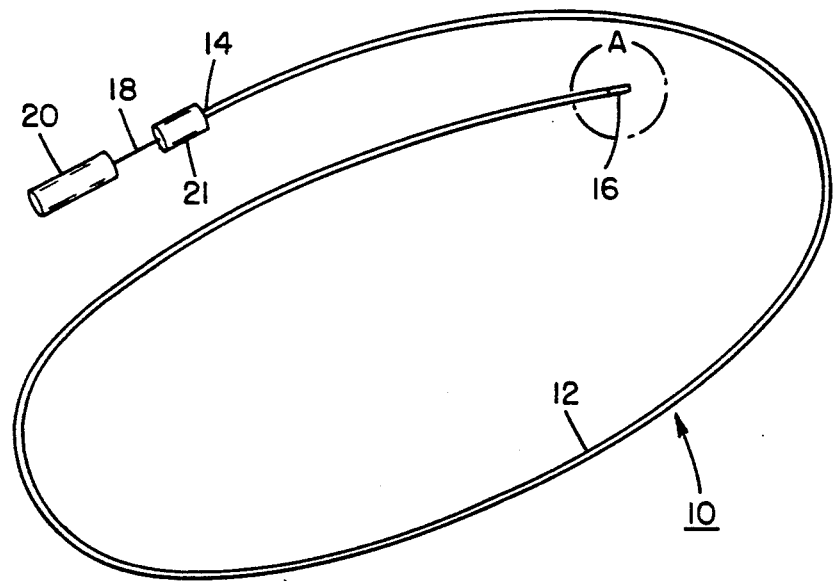
FIG. 1 illustrates a generally diagrammatic representation of a specimen sampling device for collecting microbiological biopsy specimen from a body cavity.

Referring now more specifically to FIG. 1 of the drawings, there is illustrated a specimen sampling device 10 incorporating a cytology brush which includes an elongated outer tubular portion or sheath 12 constituted from a flexible plastic material which has a proximal end 14 and a distal end 16, with the sheath 12 adapted to be inserted through the biopsy channel of an endoscope (not shown) with the distal end 16 thereof leading forwardly into the body cavity of a patient. Extending longitudinally and coaxially through the plastic sheath 12 is an operating wire 18, preferably of a medical-grade stainless steel, which has a manipulating handle or knob 20 attached to the proximal end thereof, and which extends through the full length of the outer sheathing 12 up to the distal end 16. The wire 18 is adapted to be extended forwardly into the sheath 12 until the manipulating member 20 contacts a complementary member 21 forming a limit stop on the sheath 12, with the wire 18 also being rotatable within the sheath.

Figure 2:
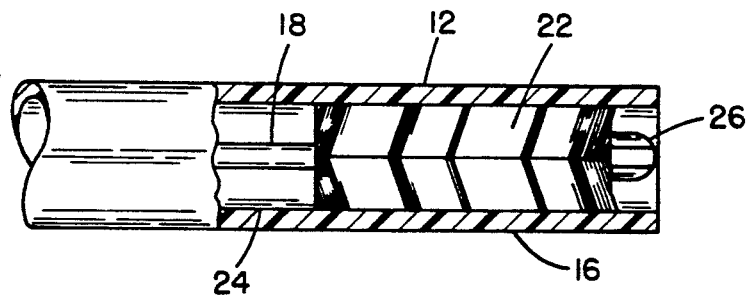
FIG. 2 illustrates, on an enlarged scale, a portion of the device of FIG. 1 in the encircled region "A", constructed pursuant to the current state-of-the-art, shown with the cytology brush in its retracted position.
Figure 3:
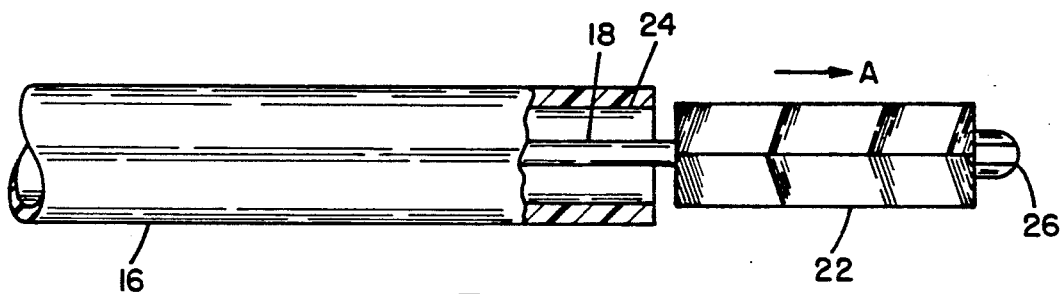
FIG. 3 illustrates the portion of the device of FIG. 2 shown with the cytology brush in its fully extended position.

As disclosed in current prior art constructions which are employed for cytology brushes, the distal end 16 of the device 10, having reference to FIG. 2 in which it is shown in its retracted position in the sheath 12, and in the fully extended operative position shown in FIG. 3 of the drawings.

Herein, the distal end of the operating wire 18 has a microbiological biopsy collector in the form of a gastrointestinal cytology brush 22 mounted thereon, with the bristles of the brush consisting of a large number of adjoiningly axial rows of bristles which radially extend into close contact with the inner wall surface 24 of the plastic sheath 12. The leading or distal end of the operating wire 18 which mounts the brush 22, the bristles of which may be constituted from nylon, has a dome-shaped or knob-like leading end 26.

The brush 22 when fully retracted into the distal end portion 16 of the sheath 12 of device 10 has the brush bristles bent over to some extent inasmuch as the outer diameters thereof are ordinarily in close contact with and slightly larger in size than the internal diameter 24 of the sheath 12. Upon being extended forwardly outwardly of the sheath 12 in the direction of arrow A as shown in FIG. 3, the radial expansion of the bristles of the brush 22 upon release from the interior of the sheath is somewhat diminished by a permanent bend imparted to the nylon bristles of the brush due to their previous confinement within the sheath 12, thereby reducing their capacity in brushing and absorbing biopsy material. Moreover, upon retraction of the cytology brush 22 into the interior of the sheath 12 subsequent to the obtention of microbiological biopsy specimen from the body cavity, this causes the bristles to again be bent to some extent and possibly causing some of the biopsy material present on the tips of the bristles to be sprayed within the body cavity, which conceivably may lead to infecting the patient. Moreover, upon withdrawal of the sampling device 10 from an endoscope, and the subsequent extension of the brush 22 in a medical laboratory in order to be able to obtain the biopsy material therefrom for analysis, can also lead to the spraying of such microbiological biopsy material, from the expanding bristles so as to possibly contaminate the environment and conceivably infect and endanger the laboratory technicians and/or medical personnel.

In order to improve upon the foregoing structure and functioning, there is provided a specimen sampling device with a cytology brush which affords the advantages of the invention, as referred to hereinabove, having specific reference to FIGS. 4 and 5 of the drawings illustrative of the distal end of the device as encircled in "A" of FIG. 1.

Figure 4:
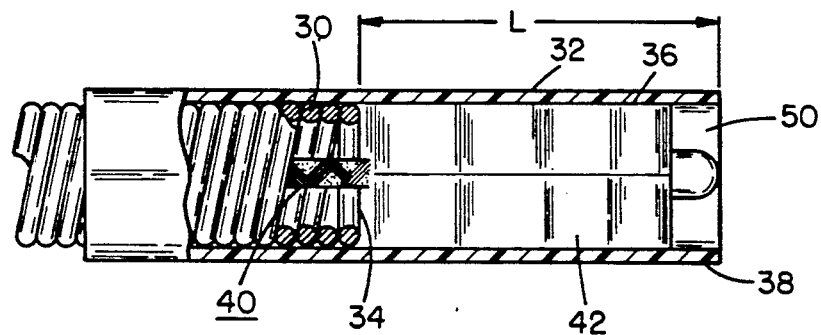
FIG. 4 illustrates a view similar to FIG. 2 of the portion of the device as constructed pursuant to the present invention shown in its retracted position.

As illustrated particularly in FIG. 4 of the drawings, the microbiological biopsy specimen sampling device includes a flexible tubular sheath 30 which is constituted of closely spaced or contiguous helical coils, preferably constituted from a medical-grade stainless steel. The flexible sheath 30 is encompassed by a resiliently flexible tubular plastic outer sleeve 32, and wherein the sheath 30 and sleeve 32 are fastened together through the intermediary of a suitable adhesive, such as an epoxy or the like. As is illustrated in the drawing, the outer sleeve 32, which may be constituted from teflon or the like, extends axially beyond the distal end 34 of the inner tubular sheath 30 by a specific distance L, and with the internal diameter 36 of the outer sheath 32, being essentially of the same size as the outer diameter 38 of the flexible steel sheath 30, which consists of the helical coils.

Extending within the tubular member 30 is the operating wire structure 40 mounting a microbiological biopsy sample collector 42 which is essentially a cytology brush having a plurality of axially closely spaced or contiguous rows of radially extending nylon bristles.

Figure 5:
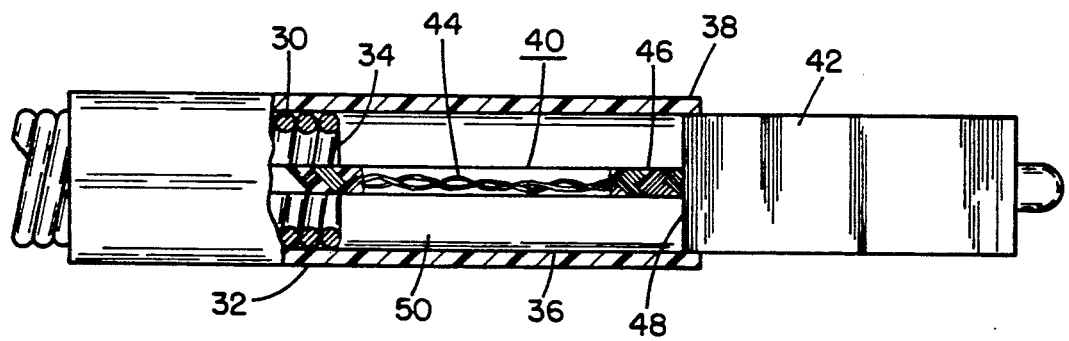
FIG. 5 illustrates a view similar to FIG. 4 shown in its fully extended operative position.

The wire structure 40 which extends coaxially within the sheath 30 and sleeve 32, as shown in cross-sectional detail in FIG. 5 essentially consists of an inner twisted wire 44 which is encompassed by a braided outer cable 46, both being formed of stainless steel, and which are fastened together at opposite ends thereof through soldering or the like so as to form an integrally rotatable and axially displaceable structure.

The cytology brush 42, which is mounted proximate the distal end of the operating wire structure 40, is dimensioned to have the outer diameter of the bristles conform with the internal diameter 36 of the outer sleeve 32 in the cylindrical section 50 present beyond the end 34 of the helically-coiled tubular sheath 30, and with the axial length of the rows of bristles of the cytology brush 42 being such as to fit completely within the axial length L of the cylindrical portion 50 formed by the outer sleeve 32.

The length of the operating wire structure 40 extending outwardly of the proximal end of the sampling device where it is connected to a suitable manipulating member (not shown) for axially shifting the cytology brush 42 and/or rotating the brush responsive to rotation being imparted to the wire structure 4 is calibrated such that the full axial forward movement of the cytology brush 42 from the cylindrical section 50 will still allow the trailing end portion 48 of the brush bristles to remain within the confines of the cylindrical section 50 of the outer sleeve 32. This will form a guidance for the brush 42 during any retraction thereof into the cylindrical section 50 subsequent to brushing and collecting microbiological biopsy specimen on the bristles from the body cavity of a patient.

Hereby, the utilization of the larger sized cylindrical section 50 of the outer sleeve 32 beyond the distal end 34 of the inner tubular sheath 20 will avoid the so-called "laying down" of the brush bristles and enable them to always remain in a fully extended radial position thereby increasing the amount of sampling material capable of being picked up by the brush, and also avoiding any spraying of material from the tips of the bristles during retraction and extension of the cytology brush 42. Additionally, the smaller internal diameter at the end 34 of the inner tubular sheath 30 in comparison with the radially larger bristles forms a stop limiting the retraction of the brush 42 indicative to an operator of the device that the brush is fully retracted in the cylindrical section 50.

The utilization of the composite operating wire structure 40 having a central twisted wire 44 which is encompassed by a braided outer cable 46 fastened thereto at the opposite ends of the sampling device also facilitates a controlled rotation of the brush 42 during operation, while concurrently the dual sheath and sleeve arrangement 30, 32 reduces the possible tendency of the device to kink during insertion into an endoscope and advance into a body cavity.

From the foregoing it thus becomes readily apparent that the sampling device for collecting microbiological biopsy specimen provides for an improved construction, the simplicity and dependable operation of which is not at all contemplated nor suggested in the current state-of-the-technology directed to such devices.

While there has been shown and described what are considered to be a preferred embodiment of the invention, it will of course, be understood that various modifications and changes in form or detail could readily be made without departing from the spirit of the invention. It is therefore intended that the invention be not limited to the exact form and detail herein shown and described, nor to anything less than the whole of the invention herein disclosed as hereinafter claimed.

What is claimed is:

1. A specimen sampling device for collecting microbiological specimen from a body cavity, said device comprising
   (a) an elongate flexible tubular member having proximal and distal ends;
   (b) an outer sleeve encompassing said tubular member, said outer sleeve being fixedly connected with said tubular member, a portion of said outer sleeve extending axially beyond the distal end of said flexible tubular member so as to form a cylindrical section having an internal diameter commensurate with the external diameter of said tubular member; and
   (c) flexible wire means extending longitudinally through said tubular member and having sample collecting means fastened thereto proximate the distal end of said tubular member; and manipulating means at the opposite end of said flexible wire means cooperating with means on the outer sleeve at the proximate end of said flexible tubular member to enable imparting a predetermined longitudinal movement to said wire means whereby in one direction of movement of said wire means said sample collecting means is fully retracted into the cylindrical section formed by space of said extended outer sleeve portion and in an opposite direction of movement of said wire means is at least partially extended from the cylindrical section of said outer sleeve so as to be exposed to enable the brushing and collecting thereof of microbiological biopsy specimen from said body cavity.

2. A specimen sampling device as claimed in claim 1, wherein said flexible tubular member comprises a sheath consisting of helical coils.

3. A specimen sampling device as claimed in claim 2, wherein said helical coil sheath is constituted from stainless steel.

4. A specimen sampling device as claimed in claim 2, wherein said outer sleeve comprises plastic tubing.

5. A specimen sampling device as claimed in claim 4, wherein said outer sleeve consists of teflon.

6. A specimen sampling device as claimed in claim 4, wherein said outer sleeve is fastened to said flexible tubular member with an epoxy adhesive.

7. A specimen sampling device as claimed in claim 1, wherein said flexible wire means for mounting said sample collecting means comprises a central wire cable having twisted wire strands; and a braided outer cable encompassing said central wire cable and axially extending therewith so as to form a coaxial woven wire sleeve, said central wire cable and said braided outer cable being fixedly interconnected proximate the distal and proximal ends thereof enabling positive rotation of said sample collecting means responsive to rotation being imparted to said manipulating means for imparting movement to said flexible wire means.

8. A specimen sampling device as claimed in claim 7, wherein said flexible wire means is constituted from stainless steel.

9. A specimen sampling device as claimed in claim 7, wherein said specimen collecting means comprises a brush.

10. A specimen sampling device as claimed in claim 9, wherein said brush comprises a plurality of axially adjacent rows of radially extending bristles having the radially inner ends fastened to said flexible wire means and radially outer ends dimensioned substantially in conformance with the inner diameter of said outer sleeve.

11. A specimen sampling device as claimed in claim 10, wherein said bristles consist of nylon.

12. A specimen sampling device as claimed in claim 10, wherein in the maximum axially forward extended position of said flexible wire means mounting said brush, the trailing rows of said bristles are located within the confines of the cylindrical section of said outer sleeve so as to guide the brush during retractive movement thereof into said outer sleeve.

13. A specimen sampling device as claimed in claim 9, wherein said brush is a cytology collector.

* * * * *